United States Patent
Kolb (10) Patent No.: US 10,067,066 B2
(45) Date of Patent: Sep. 4, 2018

(54) CONTAINER INSPECTION DEVICE AND CONTAINER INSPECTION METHOD FOR INSPECTING CONTAINERS

(71) Applicant: KRONES AG, Neutraubling (DE)

(72) Inventor: Herbert Kolb, Hausen (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 14/901,938

(22) PCT Filed: May 19, 2014

(86) PCT No.: PCT/EP2014/060260
§ 371 (c)(1),
(2) Date: Dec. 29, 2015

(87) PCT Pub. No.: WO2015/000628
PCT Pub. Date: Jan. 8, 2015

(65) Prior Publication Data
US 2016/0370299 A1 Dec. 22, 2016

(30) Foreign Application Priority Data
Jul. 1, 2013 (DE) .......................... 10 2013 106 894

(51) Int. Cl.
*G01N 21/00* (2006.01)
*G01N 21/88* (2006.01)
*G01N 21/90* (2006.01)

(52) U.S. Cl.
CPC ......... *G01N 21/8806* (2013.01); *G01N 21/90* (2013.01); *G01N 2021/8838* (2013.01)

(58) Field of Classification Search
CPC ........... G01N 21/9018; G01N 21/9036; G01N 21/8806; G01N 21/90; G01N 2021/8838
USPC .................................... 356/240.1; 250/223 B
See application file for complete search history.

(56) References Cited

U.S. PATENT DOCUMENTS

| | | | | |
|---|---|---|---|---|
| 4,380,025 | A * | 4/1983 | Deane | B07C 5/126 348/133 |
| 4,694,158 | A * | 9/1987 | Leser | B07C 5/126 209/524 |
| 2001/0054680 | A1 * | 12/2001 | Lindner | G01N 21/9036 250/223 B |
| 2004/0239878 | A1 * | 12/2004 | Bradley | A61B 5/04842 351/237 |

(Continued)

FOREIGN PATENT DOCUMENTS

DE 10017126 C1 6/2001

OTHER PUBLICATIONS

Written Opinion dated Oct. 15, 2014 of PCT/EP2014/060260.
(Continued)

*Primary Examiner* — Sunghee Y Gray
(74) *Attorney, Agent, or Firm* — Walter | Haverfield LLP; D. Peter Hochberg; Sean F. Mellino (57) ABSTRACT

A container inspection device and a container inspection device for inspecting containers are provided. The container inspection device comprises at least one light source for illuminating containers in an inspection clock for inspecting the containers. The container inspection device drives the at least one light source such that the at least one light source is observed by a person as constantly shining independent of the inspection clock.

12 Claims, 4 Drawing Sheets

(56) References Cited

U.S. PATENT DOCUMENTS

2010/0231704 A1  9/2010 Brenneman et al.
2014/0027342 A1* 1/2014 Pawlowski ............... B01L 9/06
                                                    206/570

OTHER PUBLICATIONS

International Search Report completed on Oct. 7, 2014 of PCT/EP2014/060260.
Written Opinion of PCT/EP2014/061541.
Harding, et al.; "Photic- and pattern-induced seizers: expert consensus of the epilepsy foundation of America Working Group;" Epilepsia; vol. 46, No. 9, pp. 1423-1425 (Sep. 1, 2005).

* cited by examiner

CONTAINER INSPECTION DEVICE AND CONTAINER INSPECTION METHOD FOR INSPECTING CONTAINERS

CROSS-REFERENCE TO RELATED APPLICATIONS

This application a 371 National Stage application of International Application No. PCT/EP2014/060260, filed on May 19, 2014, which claims foreign priority to German (DE) Application Serial No. 10 2013 106 894.4 filed on Jul. 1, 2013, the contents of both of which are incorporated herein by reference in their entireties.

BACKGROUND OF THE INVENTION

Field of the Invention

The present invention relates to a container inspection device and a container inspection method for inspecting containers. The container inspection device and the container inspection method can be used, for example, in a container treatment plant in which the containers are inspected by the container inspection device in respect of faults, defects, etc.

Description of the Prior Art

DE 100 17 126 C1 shows a method and a device for optically examining transparent containers. The device for performing the method comprises a LED lighting screen with a plurality LEDs which can be activated individually or in groups. The LED illuminating screen is positioned adjacent to a stream formed from a row of transparent containers positioned one after each other, a container stream. When the containers are illuminated by the LED illuminating screen, a picture of the container can be taken to perform the optical examination of the container.

Presently, in optically examining transparent containers, the light sources in a container treatment plant flash with a frequency or with a clock which corresponds to the speed of the container stream or is a multiple thereof. Herein, the light sources are configured such that they can illuminate light or shine or flash with a frequency from 0 Hz to >80 Hz.

However, it is a problem that the light sources will flash in a frequency which can cause an epileptic seizure, when the container stream has a specific speed. This is, for example, the case for a speed of 37000 containers per hour, which corresponds to a flash frequency of approximately 10.27 Hz. Due to this, persons susceptible to such an effect shall not operate in such a container treatment plant as operators.

SUMMARY OF THE PRESENT INVENTION

Therefore, it is the object of the present invention to provide a container inspection device and a container inspection method for inspecting containers with which the above-mentioned problems can be solved. In particular, a container inspection device and a container inspection method for inspecting containers shall be provided which can realize that the light source never illuminates light or shines or flashes with a frequency which can cause damages to someone's health, in particular an epileptic seizure.

This object is solved by the container inspection device for inspecting containers according to the presently claimed invention. The container inspection device comprises at least one light source for illuminating containers in an inspection clock for inspecting the containers, wherein the container inspection device is configured for driving the at least one light source such that the at least one light source is observed by a person as constantly shining independent of the inspection clock.

The light source is driven with the container inspection device such that the light source from a subjective point of view does never illuminate light or shine or flash with a frequency which can cause damages to someone's health, in particular an epileptic seizure. Thus, flash frequencies in a range around 10 Hz, in particular in the range of 3 to 15 Hz, are superimposed by at least one second flash frequency. The term "observed as constantly shining" does not mean herein that the light source actually is illuminating light or is shining constantly. Instead, the light source can also flash with a predetermined frequency, as it is explained in more detail by reference to the embodiments in the following, even when the flashing is not observable for a person unconsciously or consciously. The term "observed as constantly shining" comprises in particular that the light source is driven in particular only to flash with frequencies which are outside of the critical frequency range which can cause an epileptic seizure.

Further advantageous implementations of the container inspection device are mentioned in the dependent claims.

The control signal in the container inspection device can be configured to be dependent on at least one parameter of the light source which is to be driven. Herein, the control signal can be configured, dependent on at least one parameter of the light source to be driven, such that the power for one flash either increases and/or decreases stepwise and/or increases starting from a predetermined initial value which is different from zero. In the case that the control signal increases starting from a predetermined initial value different from zero, the additional flash signal for generating an anti-epilepsy-flash signal can be omitted as the case may be, in case the light source appears to an observer because of this such that the light source were shining continuously.

Herein, the at least one parameter of the light source to be driven can comprise the maximum frequency with which the light source to be driven can be driven and/or the maximum power and/or the maximum operating current of the light source to be driven.

Possibly, the container inspection device further comprises the control unit for controlling the light source with a control signal that superimposes a flash signal, with which the light source flashes corresponding to the inspection clock, such that a person observes the at least one light source as constantly shining or that the frequency of the light source is higher than the frequency which becomes dangerous for a human being.

The flash signal can be adjustable dependent on the speed of a container stream of a container treatment plant in which the container inspection device can be used. Herein, the control unit can be configured to output the control signal dependent thereon, whether the frequency resulting from the inspection clock and used for driving the light source is positioned in predetermined frequency range. In this case, there will be output in addition to the flash signal only an additional control signal, if it is necessary for avoiding damages to someone's health.

The predetermined frequency range can comprise frequencies which can cause an epileptic seizure for a human being. The control unit can consequently control the light source by considering this specific frequency range and can thus avoid damages caused for the health of a human being.

The above-described container inspection device can further comprise an optical detecting unit for optically detecting a predetermined container of the container stream in the inspection clock, wherein the container inspection device is configured for driving the at least one light source such that the light source in illuminating an container is regulated stepwise up to a maximum value and thereafter regulated down from the maximum value, and wherein the optical detecting unit is drivable for performing an optical detection, when the light source is illuminating with the maximum value of an illumination.

The above-described container inspection device can be part of a container treatment plant for treating of containers.

The object is further solved by a container inspection method for inspecting containers according to the presently claimed invention. The container inspection method comprises the steps: illuminating containers in a predetermined inspection clock for inspecting the containers with at least one light source, and driving the at least one light source such that the at least one light source is observed by a person as constantly shining independent of the inspection clock.

The control method achieves the same advantages as they are mentioned in respect of the control unit.

Further possible implementations of the invention also comprise combinations of features or styles described above or in the following with reference to the embodiments, even if they are not explicitly mentioned. Herein, the person skilled in the art will also add single aspects as improvements or additions to the respective basic form of the invention.

BRIEF DESCRIPTION OF THE DRAWINGS

In the following, the invention is described in more detail by means of embodiments and with reference to the appended drawing Figures, wherein.

In the figures, the same or functionally same elements are provided with the same reference signs unless given otherwise.

DETAILED DESCRIPTION OF THE PRESENT INVENTION

Figure 1:
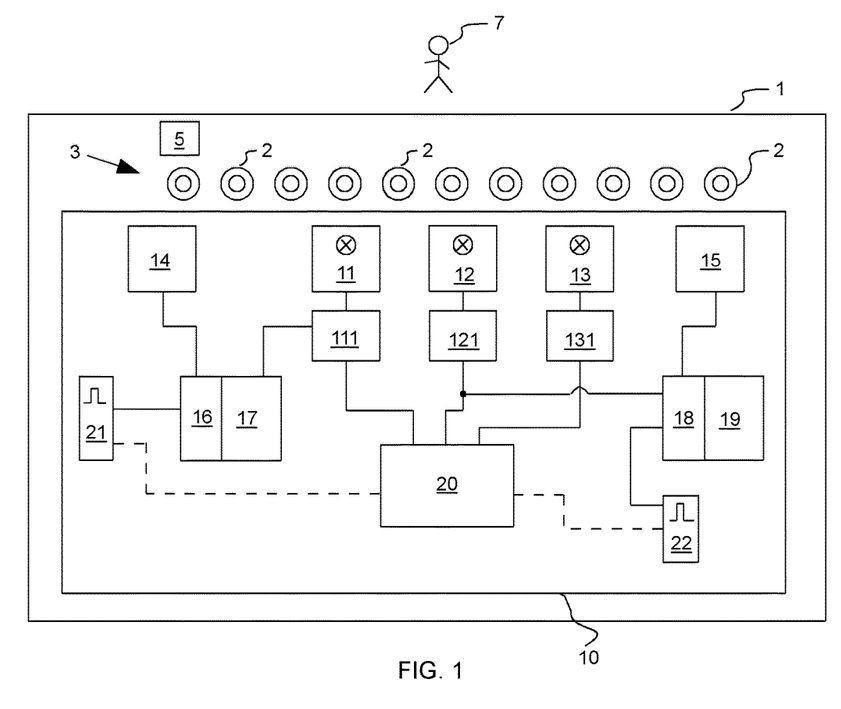
FIG. 1 shows a severely simplified view for illustrating a machine comprising a container inspection device according to a first embodiment.

FIG. 1 shows a machine 1, which can be, for example a container treatment plant, in particular an empty bottle inspection machine, a full bottle inspection machine, a label control unit, a tap inspection machine, a preform inspection machine, a filling height control machine, a stretch blow molding machine, a filling machine, a machine for treating glass containers, etc., a packing plant, a box washing plant, etc. Even if the machine 1 is described in the following partly using the example of a container treatment plant, the machine 1 will not be limited thereto.

In the machine 1, containers 2, in particular transparent plastic bottles, glass bottles, metal cans, preforms, full, empty, closed, unclosed, labeled, not labeled, etc., are produced and/or treated. It is meant therewith, that the described inspection systems can be positioned upstream or downstream of each treatment step in the container treatment plant. In FIG. 1, not all of the containers 2 are provided with reference signs for the sake of simplicity. The containers 2 are moved to pass by a container inspection device 10 in a container stream 3 in which the containers 2 are positioned each individually in a row one after another. The speed of the container stream 3 can be detected by a speed detecting unit 5. The machine 1 is, for example, operated or also only observed by a person 7.

In FIG. 1, the container inspection device 10 has a first light source 11, a second light source 12, a third light source 13, a first optical detecting unit 14, a second optical detecting unit 15, a first frame grabber 16, which is named also only first grabber 16 in the following, a first computing device 17, a second frame grabber 18, which is named also only second grabber 18 in the following, a second computing device 19, a control unit 20, a first trigger signal transducer 21, and a second trigger signal transducer 22. The first light source 11 is driven by a first light source driving unit 111. The second light source 12 is driven by a second light source driving unit 121. The third light source 13 is driven by a third light source driving unit 131.

The first and/or the second and/or the third light source(s) 11, 12, 13 illuminate(s) the containers 2 because of a driving operation by the light source driving unit(s) 111, 121, 131 such that the first and/or second optical detecting units 14, 15 can optically detect the container. In case the first and/or second optical detecting units 14, 15 are/is, for example a camera, the camera can take pictures which can be evaluated for identifying faults, defects, etc. of the containers 2.

As shown in FIG. 1, the first light source driving unit 111 is driven by the combination of the first grabber 16 and the first computing device 17. The second light source driving unit 121 is driven by the combination of the second grabber 18 and the second computing device 19. Further, the first and second light source driving units 111, 121 as well as the third light source driving unit 131 are driven by the control unit 20. The control unit 20 can also output for the first and/or second trigger signal transducer 21, 22 or receive from the first or/and trigger signal transducer 21, 22, a signal as depicted in FIG. 1 by the broken lines.

Figure 2:
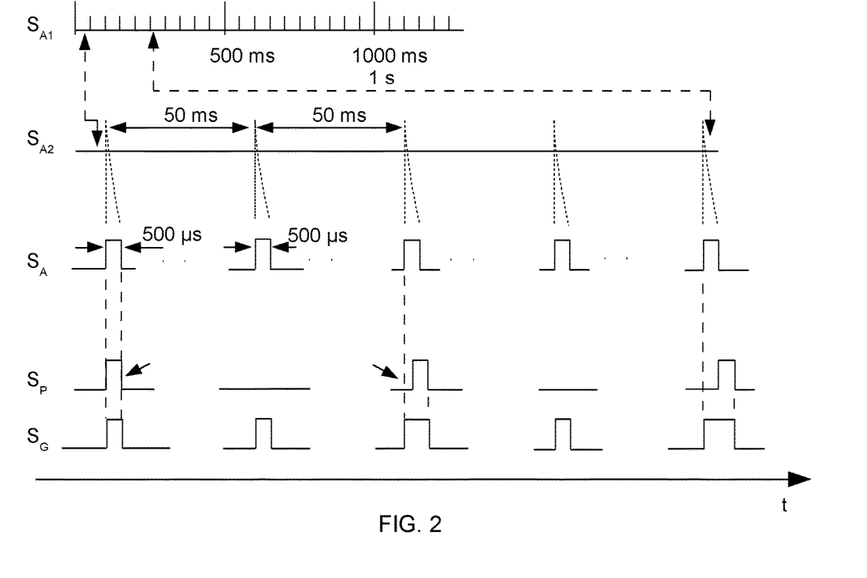
FIG. 2 shows a time chart of signals arising in the operation of the machine in a control by the control unit according to a first embodiment.

FIG. 2 shows the time chart in different time solutions. Herein, $S_{A1}$ represents an anti-epilepsy-flash signal having a frequency of 20 Hz shown in a low time resolution. $S_{A2}$ represents instead a depiction of the portion of the antiepilepsy-flash signal which is referenced with the arrows at the signal $S_{A1}$ in FIG. 3 in a somewhat higher time resolution. $S_A$ eventually refers to a depiction of the same range of the anti-epilepsy-flash signal in a further higher time resolution. For the sake of simplicity, it is always talked about the anti-epilepsy-flash signal $S_A$ before and in the following, since the signals $S_{A1}$, $S_{A2}$ are actually the same signal as the signal $S_A$. In FIG. 2 is further depicted a flash signal $S_F$ outputted from the control unit or grabber 20 and sum signal $S_G$. The flash signal $S_P$ has a clock with which the containers 2 are to be inspected. This clock is referenced also as an inspection clock of the container inspection device 10 in the following.

In FIG. 2 is shown the case that the flash signal $S_P$ has a clock which is required in a container treatment plant for illuminating the containers 2 in the case of a through put of 37000 containers per hour. Because of this clock, the flash signal $S_P$ has a frequency of approximately 10.27 Hz. This frequency is located in a predetermined frequency range in which the frequencies can cause damages to the health of a person 7, in particular an epileptic seizure. According to current knowledge, the frequency range is located in a range around 10 Hz, in particular in the range of approximately 3 to approximately 15 Hz.

Because of this reason, the control unit 20 outputs the anti-epilepsy-flash signal $S_A$ that has in FIG. 2 with 20 Hz approximately twice the frequency of the flash signal $S_P$. Therewith, the light sources 11, 12, 13 are driven in addition to the flash signal $S_P$ with the anti-epilepsy-flash signal $S_A$ for illuminating or flashing. As a result, the person 7 as the observer of the corresponding light sources 11, 12, 13 sees the sum signal $S_G$ that is depicted in FIG. 2 below the flash signal $S_P$. The person 7 will see herein the corresponding light source 11, 12, 13, as if the light source 11, 12, 13 is shining continuously. Consequently, no damages to someone's health, in particular epileptic seizures can be caused by the container treatment plant, anymore.

Figure 3:
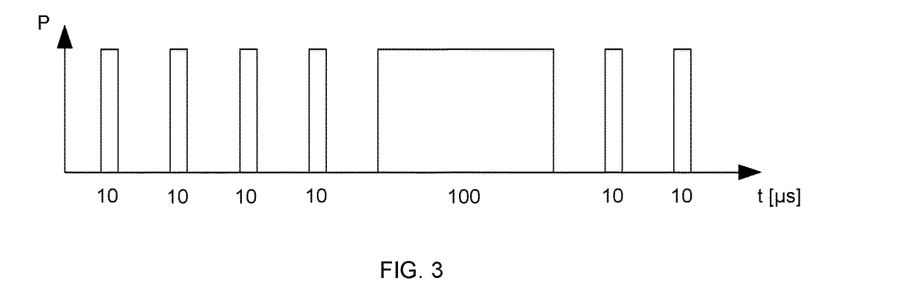
FIG. 3 shows a time chart of a further signal arising in the operation of the container inspection device according to the first embodiment.

FIG. 3 shows a further example for a sum signal $S_G$ which an observer of the respective light sources 11, 12, 13 will see in a modification of the first embodiment, if the duration of the light flashes of the anti-epilepsy-flash signal $S_A$ has a value of only approximately 10 µs. The flash signal $S_P$ is designed in this case such that the sum signal $S_G$ shown in FIG. 3 is the result for the person 7 as the observer. The person 7 will see the light source also in this case, as if the light source is shining continuously so that damages to someone's health, in particular epileptic seizures, are avoided.

Figure 4:
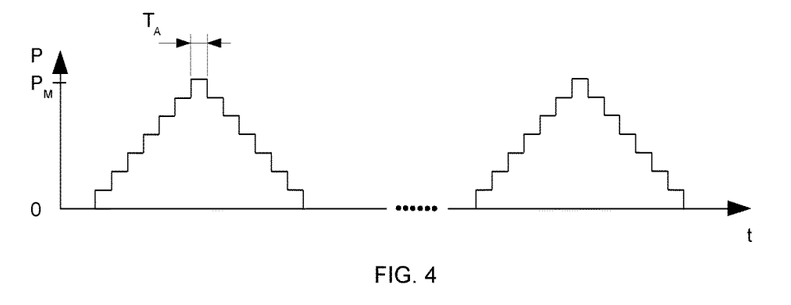
FIG. 4 shows a time chart of a signal arising in the operation of the container inspection device according to a second embodiment.

FIG. 4 shows a signal chart of a driving operation the first light source 11, the second light source 12 and the third light source 13 performed by the control unit 20 according to a second embodiment. In this embodiment, the machine 1 is implemented as described in the first embodiment. Therefore, only the differences to the first embodiment are described in the following.

Figure 5:
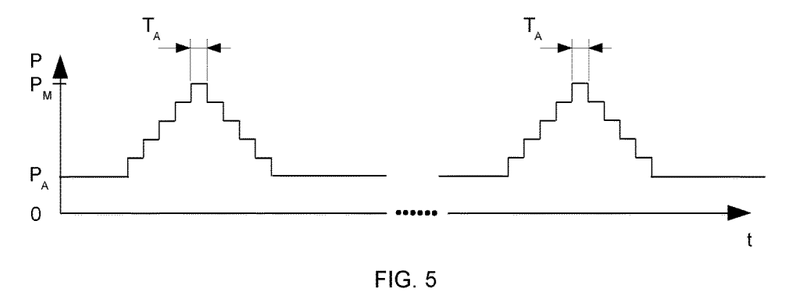
FIG. 5 shows a time chart of a signal arising in the operation of the container inspection device according to a third embodiment.

As depicted in FIG. 4, the first to third light sources 11, 12, 13 are driven by the control unit 20 by a flash signal $S_P$ such that the power P of each of the light sources of the first to third light sources 11, 12, 13 is increasing stepwise over the time t starting from the value 0. In case the power of the respective light source 11, 12, 13 increased to a predetermined value, a value $P_M$ which is a maximum for the driving, the first and/or second optical detecting units 14, 15 are driven to perform an optical detection in the recording time period $T_A$. This time is given in FIG. 5 at the highest level of the stepwise curve, namely the maximum value $P_M$. After the optical detection or at the end of the recording time period $T_A$, the control unit 20 controls the power P of each light source of the first to third light sources 11, 12, 13 such that the power P thereof decreases stepwise over the time t again to the value 0, as shown in FIG. 5. Herein, the optical detecting unit is not obliged to take a picture in every driving of the light sources 11, 12, 13.

The flash signal $S_P$ is configured preferably as shown in FIG. 4, when the frequency for driving the first to third light sources 11, 12, 13 is located inside of the predetermined frequency range because of the speed of the containers 2. Because of this the anti-epilepsy-flash signal $S_A$ can be omitted. Nevertheless, the observer will see the light source (s) 11, 12, 13, as if they are shining continuously so that damages to someone's health, in particular epileptic seizures, are avoided.

FIG. 5 shows a signal chart of a driving operation of the first light source 11, the second light source 12 and the third light source 13 performed by the control unit 20 according to a third embodiment. Also in this embodiment, the machine 1 is implemented as described in the first embodiment. Therefore, only the differences to the preceding embodiments are described in the following.

In this embodiment, the first to third light sources 11, 12, 13 are also driven stepwise over the time t as regards the power P, as described in the second embodiment. However, at least one of the light sources 11, 12, 13 is driven here by the control unit 20 such that the power P of the light source has at least one predetermined initial value $P_A$, as illustrated in FIG. 5. Further in this embodiment, the first and/or second optical detecting unit 14, 15 is driven for optical detection in each driving operation of the light sources 11, 12, 13 according to the power chart over the time t in FIG. 5. Due to this, there results the same effect as in the second embodiment so that also here the anti-epilepsy-flash signal $S_A$ can be omitted.

Figure 6:
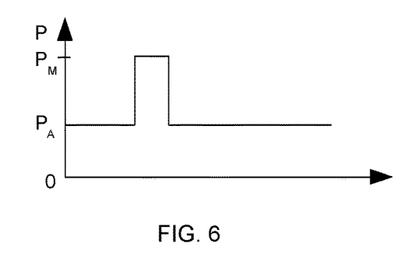
FIG. 6 shows a time chart of a signal arising in the operation of the container inspection device according to a fourth embodiment.

FIG. 6 shows a signal chart of a driving operation of the first light source 11, the second light source 12 and the third light source 13 performed by the control unit 20 according to a fourth embodiment. Also in this embodiment, the machine 1 is implemented as described in the first embodiment. Therefore, only the differences to the preceding embodiments are described in the following.

In this embodiment, the first to third light sources 11, 12, 13 are driven by a flash signal $S_P$ with a frequency as described in the first embodiment. However, here is driven at least one of the light sources 11, 12, 13 by the control unit 20 by a flash signal $S_P$ such that the power P of the light source has always over the time t a predetermined initial value $P_A$ different from zero, as illustrated in FIG. 6.

In case one of the light sources 11, 12, 13 is a LED light source, the predetermined initial value $P_A$ has a value in which the LEDs have the maximum efficiency factor. For example, the LEDs can be operated with an operating current of 10 to 20 mA for achieving the predetermined initial value $P_A$. To achieve the flash with a value above the predetermined initial value $P_A$, as shown in FIG. 6, the LEDs are then operated with an operating current of approximately 100 to 120 mA at the short time power limit.

The control signal of FIG. 6 results in the same effect as in the second and third embodiments so that the anti-epilepsy-flash signal $S_A$ can be omitted here as the case may be.

Figure 7:
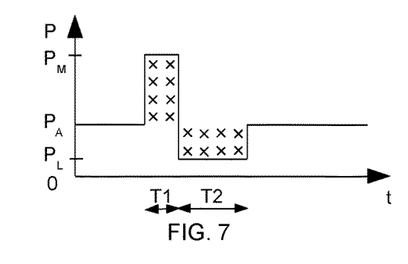
FIG. 7 shows a time chart of a signal arising in the operation of the container inspection device according to a fifth embodiment.

FIG. 7 shows a signal chart of a driving operation of the first light source 11, the second light source 12 and the third light source 13 performed by the control unit 20 according to a fifth embodiment. Also in this embodiment, the machine 1 is implemented as described in the first embodiment. Therefore, only the differences to the preceding embodiments are described in the following.

In the present embodiment, at least one of the light sources 11, 12, 13 is driven over the time t by the control unit 20 by a flash signal $S_P$ similar to the fourth embodiment in respect of its power P. Consequently, the control unit 20 controls, for example, the first light source 11 to flash, starting from the predetermined initial value $P_A$ for a predetermined first time period T1. Directly at the end of the predetermined first time period T1, the control unit 20 drives the first unit 11 such that the power P of the light source has for a predetermined second time period T2 a value $P_L$ which is smaller than the predetermined initial value $P_A$, as illustrated in FIG. 7. Herein, the regions marked in FIG. 7 with multiple x have the same space. With such a driving operation of the control unit 20 can be gained time that is necessary for recharging of capacities used in the driving.

Therewith, with such a flash signal $S_P$, can be achieved the same effect as in the fourth embodiment so that also here the anti-epilepsy-flash signal $S_A$ can be omitted as the case may be.

Figure 8:
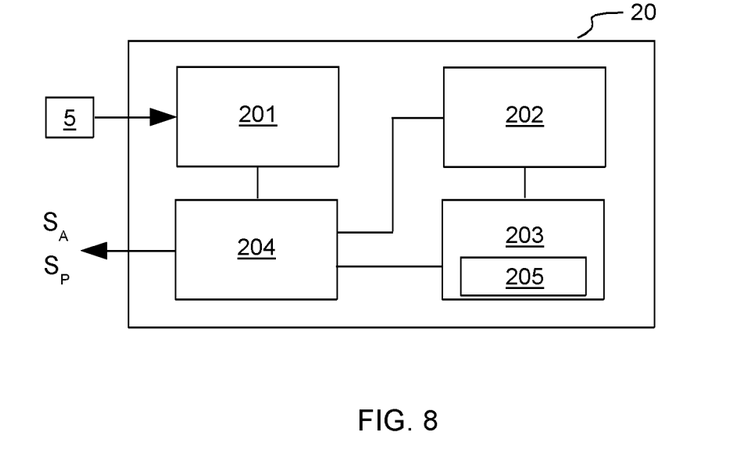
FIG. 8 shows a block diagram of a control unit of the container inspection device according to a sixth embodiment.

FIG. 8 shows the configuration of the control unit 20 according to a sixth embodiment in more detail. The control unit 20 has an ascertaining module 201, a determining module 202, a storing module 203 and an outputting module 204. Several data 205 are stored in the storing module 203.

The ascertaining module 201 ascertains with which frequency or in which clock the first to third light sources 11, 12, 13 are to be driven to illuminate predetermined containers 2 of the container stream 3 for the inspection thereof with the corresponding light source 11, 12, 13. The ascertaining module 201 can herein use a detecting result of the speed detecting unit 5 which continuously detects the speed of the containers 2 and thus the speed of the container stream 3. Alternatively, the speed detecting unit 5 can also detect the speed of a transport module for the containers 2 which is not shown. Therefore, the ascertaining module 201 can also continuously ascertain the frequency to be ascertained. The ascertaining module 201 outputs its ascertaining result, that means the frequency to be ascertained, to the outputting module 204.

The determining module 202 is configured for determining a frequency or the clock with which the individual light sources 11, 12, 13 are drivable. Herein, the determining module 202 uses parameters of the corresponding light sources 11, 12, 13 as a basis. The parameters can be, for example, the frequency which is maximally possible for driving the corresponding light source 11, 12, 13, and/or the power maximally possible for the corresponding light source 11, 12, 13 and/or the maximum operating current of the corresponding light source 11, 12, 13. The parameters are stored in the storing module 203 in the data 205. Also the determining module 202 outputs its determining result, that is the frequency to be determined, to the outputting module.

In the storing module 203 is stored in the data 205 in addition the predetermined frequency range which includes the frequencies which may cause damages to someone's health, in particular an epileptic seizure, as mentioned above.

The outputting module 204 is configured for outputting a control signal $S_A$ for controlling the corresponding light source 11, 12, 13. The control signal $S_A$ takes into account at least the predetermined frequency range and a result of an ascertainment by the ascertaining module 201. In addition, the outputting module 204 can take into account in an output of the control signal a result of a determination by the determining module 202.

For establishing the control signal $S_A$, the outputting module 204 accesses the storing module 203, in more detail, the predetermined frequency range stored in the data 205. In case the ascertaining module 201 ascertained that the frequency for driving the first to third light sources 11, 12, 13 is inside of the predetermined frequency range because of the speed of the containers 2, the outputting module 204 outputs as the control signal the anti-epilepsy-flash signal $S_A$ and/or a flash signal $S_P$ according to the container stream 3, which are explained above in respect of FIG. 2 in more detail. The flash signal $S_P$ according to the container stream 3 is referred to in the following also simply as flash signal $S_P$.

However, if the frequency or the clock for driving the first to third light sources 11, 12, 13 is outside of the predetermined frequency range, the outputting module 204 will output only a flash signal $S_P$ as control signal. The limits of the predetermined frequency range can be added as needed to the first or the second mentioned condition for fixing the control signal.

Accordingly, in all of the embodiments, the frequency of the corresponding light sources 11, 12, 13 in controlled dependent on the speed such that the light source 11, 12, 13 has such a high frequency that it looks like a constantly shining light source. In addition thereto, the control unit 20, for example in the form of a controller located between the corresponding light sources 11, 12, 13 and the respective optical detecting units 14, 15 can observe which frequency is currently necessary and which is possible. The control unit 20 then processes also because of the parameters of the corresponding light sources 11, 12,13, like maximum frequency, and frequency of the container as the containers 2, the requirements and forwards a trigger signal of high frequency to the corresponding light sources 11, 12, 13. In case this is not sufficient, for example because the container stream as the container stream 3 does not run sufficiently continuously and, thus, the corresponding light source 11, 12, 13 cannot flash due to this, since directly before a simulated triggering has taken place, also the corresponding light source 11, 12, 13 can be designed such that a frequency is possible which is twice as high than necessary.

All of the above-described implementations of the container inspection device 10, the control unit 20 and the container inspection method can be used separately or in all possible combinations thereof. In particular, an arbitrary combination of the features of the first to sixth embodiment is possible. Moreover, in particular the following modifications are conceivable.

The elements shown in the figures are depicted schematically and can differ in the specific implementation from the forms shown in the figures provided that the above-described functions are ensured.

The container inspection device 10 can comprise also only one light source, for example the first light source 11 or two light sources. Alternatively, the container inspection device 10 can also comprise more than three light sources.

Further, the container inspection device 10 can also comprise only one optical detecting unit, for example the first optical detecting unit 14. Alternatively, the container inspection device 10 can also comprise more than two optical detecting units.

The first light source 11 and/or the second light source 12 and/or the third light source 13 can be a LED light source. In the LED light source, a plurality of LEDs can be present which can be drivable individually or in groups.

In the second embodiment, the control unit 20 can also drive at least one of the light sources 11, 12, 13 such that the power P for a flash of the light source 11, 12, 13 increases continuously over the time. Moreover, the control unit 20 can also drive another light source of the light sources 11, 12, 13 such that the power of the light source 11, 12, 13 decreases continuously over the time t. Herein, other variations are conceivable, as well.

It is further possible, that the container inspection device 10 drives at least one of the light sources 11, 12, 13 such that the light source is driven in a multiple of the inspection clock, in particular a double inspection clock, to avoid the critical frequency range causing damages to someone's health.

In the second to fifth embodiment, the light sources 11, 12, 13 can be driven in the illumination of the container stream 3 with a maximum power of the light source 11, 12, 13, when the first and/or second optical detecting unit 14, 15 shall perform an optical detection.

In the sixth embodiment, the outputting module 204 can further be configured to output the control signal for controlling at least one of the light sources 11, 12, 13 dependent on the time t at which the last preceding driving operation of the light source(s) 11, 12, 13 by the control signal of the control unit 20 has taken place.

In the sixth embodiment, the outputting module 204 can also output the anti-epilepsy-flash signal $S_A$ in case the frequency for driving the first to third light source 11, 12, 13 is located outside of the predetermined frequency range.

In addition, at least one of the light sources 11, 12, 13 can comprise at least one segment which is always switched on in the operation of the container inspection device 10 unless the corresponding light source 11, 12, 13 is activated to flash. The segment can also be referred to as anti-epilepsy-segment. The segment can comprise suitable illuminating means as for example LED and/or at least one other illumination appliance. Likewise, it can be active permanently to provide for a certain base lightness.

In addition, the storing module 203 does not have to be a part of the control unit 20 in the sixth embodiment. The storing module 203 can also be an external storing unit, which the storing unit 20 can access.

Having described preferred embodiments of the invention, it will be apparent to those skilled in the art to which this invention relates, that modifications and amendments to various features and items can be effected and yet still come within the general concept of the invention. It is to be understood that all such modifications and amendments are intended to be included within the scope of the present invention.

What is claimed is:

1. A container inspection device for inspecting containers, the container inspection device comprising:
    at least one light source for illuminating containers when the containers move to pass by the at least one light source one after another, and
    an ascertaining module for ascertaining a sequence of illumination times at which the at least one light source is to be driven to illuminate predetermined containers for the inspection of the predetermined containers one after another,
    wherein the container inspection device is configured for driving the at least one light source dependent on the ascertained sequence of illumination times, and
    wherein if the ascertained sequence of illumination times has a frequency <15 Hz, the container inspection device is configured for driving the at least one light source such that the at least one light source flashes with a flash frequency of at least 15 Hz independent from flashes for the ascertained sequence of illumination times to inspect the predetermined containers, and
    wherein if the ascertained sequence of illumination times has a frequency ≥15 Hz, the container inspection device is configured for driving the at least one light source such that the at least one light source flashes with the ascertained sequence of illumination times to inspect the predetermined containers.

2. The container inspection device according to claim 1, wherein a control signal ($S_A$) is dependent on at least one parameter of the light source which is to be driven.

3. The container inspection device according to claim 2, wherein the at least one parameter of the light source to be driven comprises the maximum frequency with which the light source to be driven can be driven and/or the maximum power and/or the maximum operating current of the light source to be driven.

4. The container inspection device according to claim 1, wherein a control signal ($S_A$) is configured, dependent on at least one parameter of the light source to be driven, such that the power for one flash either increases and/or decreases stepwise and/or increases starting from a predetermined initial value ($P_A$) which is different from zero.

5. The container inspection device according to claim 1, further comprising a control unit for controlling the light source with a control signal ($S_A$) that has the flash frequency which is superimposed to the frequency of a flash signal ($S_P$), with which the light source flashes corresponding to the ascertained sequence of illumination times, such that a person observes the at least one light source as constantly shining.

6. The container inspection device according to claim 5, wherein the control unit is configured to output the control signal ($S_A$) dependent thereon, whether the ascertained sequence of illumination times has a frequency <15 Hz.

7. The container inspection device according to claim 1, wherein the ascertaining module is configured for continuously ascertaining the sequence of illumination times by using a detecting result of a speed detecting unit which continuously detects the speed of a container stream of a container treatment plant in which the container inspection device is usable.

8. The container inspection device according to claim 1, wherein the frequency <15 Hz comprises frequencies which can cause an epileptic seizure for a person.

9. The container inspection device according to claim 1, further comprising an optical detecting unit for optically detecting a predetermined container of the container stream in the inspection clock,
    wherein the control unit is configured for driving the at least one light source such that the light source in illuminating a container is regulated stepwise up to a maximum value ($P_M$) and thereafter regulated down from the maximum value ($P_M$), and
    wherein the optical detecting unit is drivable for performing an optical detection, when the light source is illuminating with the maximum value ($P_M$) of an illumination.

10. The container inspection device according to claim 1, wherein the container inspection device is at least one selected from the group consisting of an empty bottle inspection device, a full bottle inspection device and an inspection device for inspecting the labels of the containers.

11. A container treatment plant for treating of containers, comprising a container inspection device for inspecting containers, the container inspection device comprising:
    at least one light source for illuminating containers, when the containers move to pass by the at least one light source one after another, and
    an ascertaining module for ascertaining a sequence of illumination times at which the at least one light source is to be driven to illuminate predetermined containers for the inspection of the predetermined containers one after another, wherein the container inspection device is configured for driving the at least one light source dependent on the ascertained sequence of illumination times, and wherein if the ascertained sequence of illumination times has a frequency <15 Hz, the container inspection device is configured for driving the at least one light source such that the at least one light source flashes with a flash frequency of at least 15 Hz independent from flashes for the ascertained sequence of illumination times to inspect the predetermined containers, and wherein if the ascertained sequence of illumination times has a frequency ≥15 Hz, the container inspection device is configured for driving the at least one light source such that the at least one light source flashes with the ascertained sequence of illumination times to inspect the predetermined containers.

12. A container inspection method for inspecting containers, the container inspection method comprising the following steps:

illuminating containers with at least one light source, when the containers move to pass by the at least one light source one after another;

ascertaining, by an ascertaining module, a sequence of illumination times at which the at least one light source is to be driven to illuminate predetermined containers for the inspection of the predetermined containers one after another, and driving the at least one light source dependent on the ascertained sequence of illumination times, wherein if the ascertained sequence of illumination times has a frequency <15 Hz, the container inspection device drives at least one light source such that the at least one light source flashes with a flash frequency of at least 15 Hz, independent from flashes for the ascertained sequence of illumination times to inspect the predetermined containers, and wherein if the ascertained sequence of illumination times has a frequency of ≥15 Hz, the container inspection device is configured for driving the at least one light source such that the at least one light source flashes with the ascertained sequence of illumination times to inspect the predetermined containers.

* * * * *